(12) United States Patent
Lightner et al.

(10) Patent No.: US 7,476,779 B2
(45) Date of Patent: Jan. 13, 2009

(54) GENERATION OF PLANTS WITH ALTERED OIL CONTENT

(75) Inventors: Jonathan Lightner, Des Moines, IA (US); Jeremy E. Coate, Ithaca, NY (US); Stephanie K. Clendennen, Kingsport, TN (US); Nancy Anne Federspiel, Menlo Park, CA (US); Debra K. Schuster, Portland, OR (US)

(73) Assignee: Agrinomics LLC, Portland, OR (US)

( * ) Notice: Subject to any disclaimer, the term of this patent is extended or adjusted under 35 U.S.C. 154(b) by 407 days.

(21) Appl. No.: 10/508,442

(22) PCT Filed: Mar. 19, 2003

(86) PCT No.: PCT/US03/08739

§ 371 (c)(1),
(2), (4) Date: May 18, 2005

(87) PCT Pub. No.: WO03/079766

PCT Pub. Date: Oct. 2, 2003

(65) Prior Publication Data

US 2005/0257288 A1    Nov. 17, 2005

Related U.S. Application Data

(60) Provisional application No. 60/366,108, filed on Mar. 20, 2002.

(51) Int. Cl.
*A01H 5/00* (2006.01)
*C12N 15/82* (2006.01)

(52) U.S. Cl. ........................... 800/281; 800/298
(58) Field of Classification Search ................ None
See application file for complete search history.

(56) References Cited

U.S. PATENT DOCUMENTS

| | | | |
|---|---|---|---|
| 5,639,790 A | 6/1997 | Voelker et al. | |
| 5,704,160 A | 1/1998 | Bergquist et al. | |
| 6,229,033 B1 | 5/2001 | Knowlton | |
| 6,248,939 B1 | 6/2001 | Leto et al. | |
| 7,135,618 B2 * | 11/2006 | Mittendorf et al. | 800/281 |

FOREIGN PATENT DOCUMENTS

| WO | WO01/083697 | 11/2001 |
|---|---|---|
| WO | WO 02/04648 | 1/2002 |

OTHER PUBLICATIONS

Baulcombe, D., Archives of Virology, Arch Virol (1999) [Suppl] 15: 189-201.
Eastmond, et al., Re-examining the role of the glyoxylate cycle in oilseeds, Trends in Plant Science vol. 6 No. 2 (2001).
Eastmond, et al., Postgerminative growth and lipid catabolism in oilseeds lacking the glyoxylate cycle, PNAS, (2000) vol. 97, No. 10, 5669-5674.
Olsen, et al., Targeting of glyoxysomal proteins to peroxisomes in leaves and roots of a higher plant (1993) The Plant Cell, vol. 5, 941-952.
Sato, et al., Structural analysis of Arabidopsis thaliana chromosome 3. 1., Sequence features of the regions of 4,504,864 bp covered by sixty P1 and TAC clones, Isocitrate lyase, Genbank reference P28297.
Eccleston and Ohirogge, "Expression of Lauroyl-Acyl Carrier Protein Thioesterase in *Brassica napus* Seeds Induces Pathways for Both Fatty Acid Oxidation and Biosynthesis and Implies a Set Point for Triacylglycerol Accumulation," *The Plant Cell*, 10(4):613-621, 1998.
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "Arabidopsis genes involved in acyl lipid metabolism. A 2003 census of the candidates, a study of the distribution of expressed sequence tags in organs, and a web-based database," *Plant Physiol.*, 132:681-697, 2003.
Dehesh et al., "Overexpression of 3-ketoacyl-acyl-carrier protein synthase IIIs in plants reduces the rate of lipid synthesis," *Plant Physiol.*, 125:1103-1114, 2001.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in Arabidopsis," *The Plant Cell*, 17:182-203, 2005.
Focks and Benning, "*wrinkled1*: A novel, low-seed-oil mutant of Arabidopsis with a deficiency in the seed-specific regulation of carbohydrate metabolism," *Plant Physiol.*, 118:91-101, 1998.
Girke et al., "Microarray analysis of developing Arabidopsis seeds," *Plant Physiol.*, 124:1570-1581, 2000.
Katavic et al., "Utility of the *Arabidopsis FAE1* and yeast *SLC1-1* genes for improvements in erucic acid and oil content in rapeseed," *Biochem Soc. Trans.*, 28(6):935-937, 2000.
Larson et al., "Acyl CoA profiles of transgenic plants that accumulate medium-chain fatty acids indicate inefficient storage lipid synthesis in developing oilseeds," *The Plant Journal*, 32:519-527, 2002.
Lin et al., "The Pex16p homolog SSE1 and storage organelle formation in *Arabidopsis* seeds," *Science*. 284;328-330, 1999.
Liu and Butow, "A transcriptional switch in the expression of yeast tricarboxylic acid cycle genes in response to a reduction or loss of respiratory function," *Mol. Cell. Biol.*, 19:6720-6728, 1999.
Mekhedov et al., "Toward a functional catalog of the plant genome. A survey of genes for lipid biosynthesis," *Plant Physiol.*, 122:389-401, 2000.
Moire et al., "Impact of unusual fatty acid synthesis on futile cycling through β-oxidation and on gene expression in transgenic plants," *Plant Physiol.*, 134:432-442, 2004.
Neuhaus and Emes, "Nonphotosynthetic Metabolism In Plastids," *Annu. Rev. Plant Physiol. Plant Mol. Biol.*, 51:111-140, 2000.
O'Hara et al., "Fatty acid and lipid biosynthetic genes are expressed at constant molar ratios but different absolute levels during embryogenesis," *Plant Physiol.*, 129:310-320, 2002.

(Continued)

*Primary Examiner*—Elizabeth F McElwain
(74) *Attorney, Agent, or Firm*—Klarquist Sparkman, LLP

(57) ABSTRACT

The present invention is directed to plants that display an altered oil content phenotype due to altered expression of an ICL nucleic acid. The invention is further directed to methods of generating plants with an altered oil content phenotype.

13 Claims, No Drawings

OTHER PUBLICATIONS

Pritchard et al., "Germination and storage reserve mobilization are regulated independently in *Arabidopsis*," *The Plant Journal*, 31(5):639-647, 2002.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:Citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during Arabidopsis seed filling," *The Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al., "Characterization of an acyl-CoA synthetase from *Arabidopsis thaliana*," *Biochem Soc.Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in Brassicaceae oilseeds," *Biochem. Soc. Trans.*, 28(6):595-598, 2000.

White et al., "A new set of Arabidopsis expressed sequence tags from developing seeds. The metabolic pathway from carbohydrates to seed oil," *Plant Physiol.*, 124:1582-1594, 2000.

Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.

Colbert et al., "High-throughput screening for induced point mutations," *Plant Physiol.*, 126(2):480-484, 2001.

Feldmann et al., "A Dwarf Mutant of Arabidopsis Generated by T-DNA Insertion Mutagenesis," *Science*, 243(4896):1351-1354, 1989.

Jako et al., "Seed-specific over-expression of an Arabidopsis cDNA encoding a diacylglycerol acyltransferase enhances seed oil content and seed weight," *Plant Physiol.*, 126(2):861-874, 2001.

James and Dooner, "Isolation of EMS-induced mutants in Arabidopsis altered in seed fatty acid composition," *Theor. Appl. Genet.*, 80(2):241-245, 1990.

Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.

Lemieux et al., "Mutants of Arabidopsis with alterations in seed lipid fatty acid composition," *Theor. Appl. Genet.*, 80(2):234-240, 1990.

Lionneton et al., "Development of an AFLP-based linkage map and localization of QTLs for seed fatty acid content in condiment mustard (*Brassica juncea*)," *Genome*, 45(6):1203-1215, 2002.

McCallum et al., "Targeted screening for induced mutations," *Nat. Biotechnol.*, 18(4):455-457, 2000.

Okuley et al., "Arabidopsis FAD2 Gene Encodes the Enzyme That Is Essential for Polyunsaturated Lipid Synthesis," *Plant Cell*, 6:147-158, 1994.

Wada et al., "Role of a positive regulator of root hair development, CAPRICE, in Arabidopsis root epidermal cell differentiation," *Development*, 129(23):5409-5419, 2002.

Yadav et al., "Cloning of higher plant omega-3 fatty acid desaturases," *Plant Physiol.*, 103(2):467-476, 1993.

\* cited by examiner

GENERATION OF PLANTS WITH ALTERED OIL CONTENT

REFERENCE TO RELATED APPLICATIONS

This application claims priority to U.S. provisional patent application 60/366,108 filed on Mar. 20, 2002. The content of the prior application is hereby incorporated in its entirety.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the US soybean crop is crushed by the soy processing industry. Soy processing yields purified oil, which is sold at high value, while the remainder is sold principally for lower value livestock feed (US Soybean Board, 2001 Soy Stats). Canola seed is crushed to produce oil and the co-product canola meal (Canola Council of Canada). Nearly 20% of the 1999/2000 US corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many fed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from ~3.5% to ~7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No.: 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990; James and Dooner, 1990). T-DNA mutagenesis screens (Feldmann et al., 1989) that detected altered fatty acid composition identified the omega 3 desaturase (FAD3) and delta-12 desaturase (FAD2) genes (U.S. Pat. No. 5952544; Yadav et al., 1993; Okuley et al., 1994). A screen which focused on oil content rather than oil quality, analyzed chemically-induced mutants for wrinkled seeds or altered seed density, from which altered seed oil content was inferred (Focks and Benning, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, 1995). It was further shown that seed-specific over-expression of the DGAT cDNA was associated with increased seed oil content (Jako et al., 2001).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992; Weigel et al. 2000). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis,* to identify many different kinds of mutant phenotypes and the genes associated with these phenotypes (Wilson et al., 1996, Schaffer et al., 1998, Fridborg et al., 1999; Kardailsky et al., 1999).

We used activation tagging techniques to identify the association between *Arabidopsis* isocitrate lyase (ICL) and an altered oil content phenotype. Isocitrate lyase (EC: 4.1.3.1) is an enzyme that catalyzes the conversion of isocitrate to succinate and glyoxylate. This is the first step in the glyoxylate bypass, a specialized metabolic pathway that serves as an alternative to the tricarboxylic acid cycle in bacteria, fungi and plants. *Arabidopsis* ICL mutants have been isolated that are deficient in the glyoxylate cycle, which plays a central role in the use of stored oil in oilseeds (Eastmond and Graham, 2000, Trends Plant Sci 6:72-8; Eastmond et al. 2001, Proc Natl Acad Sci USA 97:5669-74).

SUMMARY OF THE INVENTION

The present invention provides a method of producing an altered oil content phenotype in a plant. The method comprises introducing into plant progenitor cells a vector comprising a nucleotide sequence that encodes or is complementary to a sequence encoding an ICL polypeptide and growing a transgenic plant that expresses the nucleotide sequence. In one embodiment, the ICL polypeptide has at least 50% sequence identity to the amino acid sequence presented in SEQ ID NO:2 and comprises an isocitrate lyase domain. In other embodiments, the ICL polypeptide has at least 80% or 90% sequence identity to or has the amino acid sequence presented in SEQ ID NO:2.

In one preferred embodiment of the invention, the altered oil content phenotype is a high oil phenotype.

The invention further provides plants, plant parts, and oils obtained by the methods described herein. Preferred plants include rapeseed, soy, corn, sunflower, cotton, cocoa, safflower, oil palm, coconut palm, flax, castor and peanut. Preferred plant parts include seeds.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., 1989, and Ausubel FM et al., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality. An "altered oil content phenotype" refers to measurable phenotype of a genetically modified plant, where the plant displays an increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes reference to a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Identification of Plants with an Altered Oil Content Phenotype

We used an *Arabidopsis* activation tagging screen to identify the association between the gene encoding an isocitrate lyase (ICL), and an altered oil content phenotype (specifically, a high oil phenotype). Briefly, and as further described in the Examples, a large number of *Arabidopsis* plants were mutated with the pSKI015 vector, which comprises a T-DNA from the Ti plasmid of *Agrobacterium tumifaciens,* a viral enhancer element, and a selectable marker gene (Weigel et al, 2000). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 15-20 T2 seeds were collected from transformed T1 plants, and lipids were extracted from whole seeds. Gas chromatography (GC) analysis was performed to determine fatty acid content and composition of seed samples.

An *Arabidopsis* line that showed a high-oil phenotype, was identified, wherein oils (i.e., fatty acids) constituted approximately 37% of seed mass. The association of the ICL gene with the high oil phenotype was discovered by analysis of the genomic DNA sequence flanking the T-DNA insertion in the identified line. Accordingly, ICL genes and/or polypeptides may be employed in the development of genetically modified plants having a modified oil content phenotype. ICL genes may be used in the generation of oilseed crops that provide improved oil yield from oilseed processing and in the generation of feed grain crops that provide increased energy for animal feeding. ICL genes may further be used to increase the oil content of specialty oil crops, in order to augment yield of desired unusual fatty acids.

ICL Nucleic Acids and Polypeptides

*Arabidopsis* ICL nucleic acid (cds) sequence is provided in SEQ ID NO:1 and in Genbank entry GI 4589440, complement of nucleotides 12755-12726, 12609-12203, 11579-10977, 10700-10108, 9768-9671. The corresponding protein sequence is provided in SEQ ID NO:2 and in GI 11994639.

As used herein, the term "ICL polypeptide" refers to a fill-length ICL protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active ICL polypeptide causes an altered oil content phenotype when mis-expressed in a plant. In a further preferred embodiment, mis-expression of the ICL polypeptide causes a high oil phenotype in a plant. In another embodiment, a functionally active ICL polypeptide is capable of rescuing defective (including deficient) endogenous ICL activity when expressed in a plant or in plant cells; the rescuing polypeptide may be from the same or from a different species as that with defective activity. In another embodiment, a functionally active fragment of a full length ICL polypeptide (i.e., a native polypeptide having the sequence of SEQ ID NO:2 or a naturally occurring ortholog thereof) retains one of more of the biological properties associated with the full-length ICL polypeptide, such as signaling activity, binding activity, catalytic activity, or cellular or extra-cellular localizing activity. Preferred ICL polypeptides display enzymatic (isocitrate lyase) activity. An ICL fragment preferably comprises an ICL domain, such as a C- or N-terminal or catalytic domain, among others, and preferably comprises at least 10, preferably at least 20, more preferably at least 25, and most preferably at least 50 contiguous amino acids of an ICL protein. Functional domains can be identified using the PFAM program (Bateman A et al., 1999 Nucleic Acids Res 27:260-262; website at pfan.wustl.edu). A preferred ICL fragment comprises an ICL domain (PF00463). The ICL domain of SEQ ED NO:2 is found at approximately amino acid residues 26-551. Functionally active variants of full-length ICL polypeptides or fragments thereof include polypeptides with amino acid insertions, deletions, or substitutions that retain one of more of the biological properties associated with the full-length ICL polypeptide. In some cases, variants are generated that change the post-translational processing of an ICL polypeptide. For instance, variants may have altered protein transport or protein localization characteristics or altered protein half-life compared to the native polypeptide.

As used herein, the term "ICL nucleic acid" encompasses nucleic acids with the sequence provided in or complementary to the sequence provided in SEQ ID NO:1, as well as functionally active fragments, derivatives, or orthologs thereof. An ICL nucleic acid of this invention may be DNA, derived from genomic DNA or cDNA, or RNA.

In one embodiment, a functionally active ICL nucleic acid encodes or is complementary to a nucleic acid that encodes a functionally active ICL polypeptide. Included within this definition is genomic DNA that serves as a template for a primary RNA transcript (i.e., an mRNA precursor) that requires processing, such as splicing, before encoding the functionally active ICL polypeptide. An ICL nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed ICL polypeptide, or an intermediate form. An ICL polynucleotide can also include heterologous coding sequences, for example, sequences that encode a marker included to facilitate the purification of the fused polypeptide, or a transformation marker.

In another embodiment, a functionally active ICL nucleic acid is capable of being used in the generation of loss-of-function ICL phenotypes, for instance, via antisense suppression, co-suppression, etc.

In one preferred embodiment, an ICL nucleic acid used in the methods of this invention comprises a nucleic acid sequence that encodes or is complementary to a sequence that encodes an ICL polypeptide having at least 50%, 60%, 70%, 75%, 80%, 85%, 90%, 95% or more sequence identity to the polypeptide sequence presented in SEQ ID NO:2.

In another embodiment an ICL polypeptide of the invention comprises a polypeptide sequence with at least 50% or 60% identity to the ICL polypeptide sequence of SEQ ID NO:2, and may have at least 70%, 80%, 85%, 90% or 95% or more sequence identity to the ICL polypeptide sequence of SEQ ID NO:2. In another embodiment, an ICL polypeptide comprises a polypeptide sequence with at least 50%, 60%, 70%, 80%, 85%, 90% or 95% or more sequence identity to a functionally active fragment of the polypeptide presented in SEQ ID NO:2, such as an ICL domain. In yet another embodiment, an ICL polypeptide comprises a polypeptide sequence with at least 50%, 60 %, 70%, 80%, or 90% identity to the polypeptide sequence of SEQ ID NO:2 over its entire length and comprises an ICL domain.

In another aspect, an ICL polynucleotide sequence is at least 50% to 60% identical over its entire length to the ICL nucleic acid sequence presented as SEQ ID NO: 1, or nucleic acid sequences that are complementary to such an ICL sequence, and may comprise at least 70%, 80%, 85%, 90% or 95% or more sequence identity to the ICL sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410; website at blast.wustl.edu/blast README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate). In other embodiments, moderately stringent hybridization conditions are used that comprise: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding an ICL polypeptide can be produced. For example, codons may be selected to increase the rate at which expression of the polypeptide occurs in a particular host species, in accordance with the optimum codon usage dictated by the particular host organism (see, e.g., Nakamura et al., 1999). Such sequence variants may be used in the methods of this invention.

The methods of the invention may use orthologs of the *Arabidopsis* ICL. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis,* may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen MA and Bork P, Proc Natl Acad Sci (1998) 95:5849-

5856; Haynen M A et al., Genome Research (2000) 10:1204-1210). Programs for multiple sequence alignment, such as CLUSTAL (Thompson J D et al., 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989; Dieffenbach and Dveksler, 1989). For instance, methods for generating a cDNA library from the plant species of interest and probing the library with partially homologous gene probes are described in Sambrook et al. A highly conserved portion of the *Arabidopsis* ICL coding sequence may be used as a probe. ICL ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known ICL polypeptides are used for ortholog isolation (see, e.g., Harlow and Lane, 1988, 1999). Western blot analysis can determine that an ICL ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which ICL nucleic acid and/or polypeptide sequences have been identified.

ICL nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991), may be used to introduce desired changes into a cloned nucleic acid In general, the methods of the invention involve incorporating the desired form of the ICL nucleic acid into a plant expression vector for transformation of in plant cells, and the ICL polypeptide is expressed in the host plant.

An isolated ICL nucleic acid molecule is other than in the form or setting in which it is found in nature and is identified and separated from least one contaminant nucleic acid molecule with which it is ordinarily associated in the natural source of the ICL nucleic acid. However, an isolated ICL nucleic acid molecule includes ICL nucleic acid molecules contained in cells that ordinarily express ICL where, for example, the nucleic acid molecule is in a chromosomal location different from that of natural cells.

Generation of Genetically Modified Plants with an Altered Oil Content Phenotype

ICL nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the ICL gene in a plant is used to generate plants with a high oil phenotype.

The methods described herein are generally applicable to all plants. Although activation tagging and gene identification is carried out in *Arabidopsis,* the ICL gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an ICL polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., 1989), sunflower Everett et al, 1987), and soybean (Christou et al., 1989; Kline et al., 1987).

Expression (including transcription and translation) of ICL may be regulated with respect to the level of expression, the tissue type(s) where expression takes place and/or developmental stage of expression. A number of heterologous regulatory sequences (e.g., promoters and enhancers) are available for controlling the expression of an ICL nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al, 1992), the CsVMV promoter (Verdaguer B et al., 1998) and the melon actin promoter (published PCT application WO0056863). Exemplary tissue-specific promoters include the tomato E4 and E8 promoters (U.S. Pat. No. 5,859, 330) and the tomato 2AII gene promoter (Van Haaren M J J et al., 1993).

In one preferred embodiment, ICL expression is under control of regulatory sequences from genes whose expression is associated with early seed and/or embryo development. Legume genes whose promoters are associated with early seed and embryo development include *V. faba legumin* (Baumlein et al., 1991, Mol Gen Genet 225:121-8; Baumlein et al., 1992, Plant J 2:233-9), *V. faba usp* (Fiedler et al., 1993, Plant Mol Biol 22:669-79), pea convicilin (Bown et al., 1988, Biochem J 251:717-26), pea lectin (dePater et al., 1993, Plant Cell 5:877-86), *P. vulgaris* beta phaseolin (Bustos et al., 1991, EMBO J 10:1469-79), *P. vulgaris* DLEC2 and *PHS* [beta] (Bobb et al., 1997, Nucleic Acids Res 25:641-7), and soybean beta-Conglycinin, 7S storage protein (Chamberland et al., 1992, Plant Mol Biol 19:937-49). Cereal genes whose promoters are associated with early seed and embryo development include rice glutelin ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice prolamin (Zhou & Fan, 1993, Transgenic Res 2:141-6), wheat prolamin (Hammond-Kosack et al., 1993, EMBO J 12:545-54), maize zein (Z4, Matzke et al., 1990, Plant Mol Biol 14:323-32), and barley *B-hordeins* (Entwistle et al., 1991, Plant Mol Biol 17:1217-31). Other genes whose promoters are associated with early seed and embryo development include oil palm GLO7A (7S globulin, Morcillo et al., 2001, Physiol Plant 112:233-243), *Brassica napus napin*, 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus oleosin* (Keddie et al., 1994, Plant Mol Biol 24:32740), *Arabidopsis oleosin* (Plant et al., 1994, Plant Mol Biol 25:193-205), *Arabidopsis FAE1* (Rossak et al., 2001, Plant Mol Biol 46:717-25), *Canavalia gladiata* conA (Yamamoto et al., 1995, Plant Mol Biol 27:729-41), and *Catharanthus roseus* strictosidine synthase (Str, Ouwerkerk and Memelink, 1999, Mol Gen Genet 261:635-43). In another preferred embodiment, regulatory sequences from genes expressed during oil biosynthesis are used (see, e.g., U.S. Pat. No.: 5,952,544). Alternative promoters are from plant storage protein genes (Bevan et al., 1993, Philos Trans R Soc Lond B Biol Sci 342:209-15).

In yet another aspect, in some cases it may be desirable to inhibit the expression of endogenous ICL in a host cell. Exemplary methods for practicing this aspect of the invention include, but are not limited to antisense suppression (Smith, et al.,1988; van der Krol et al., 1988); co-suppression (Napoli, et al., 1990); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988), a partial cDNA sequence including fragments of 5' coding sequence, (Cannon et al., 1990), or 3' non-coding sequences (Ch'ng et al., 1989). Cosuppression techniques may use the entire cDNA sequence (Napoli et al., 1990; van der Krol et al., 1990), or a partial cDNA sequence (Smith et al., 1990).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Plants with a High Oil Phenotype by Transformation with an Activation Tagging Construct Mutants were generated using the activation tagging "ACTTAG" vector, pSKI015 (GI 6537289; Weigel et al., 2000). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance. T2 seed was collected from T1 plants and stored in an indexed collection, and a portion of the T2 seed was accessed for the screen.

Quantitative determination of seed fatty acid content was performed using the follows methods. An aliquot of 15 to 20 T2 seeds from each line tested, which generally contained homozygous insertion, homozygous wild-type, and heterozygous genotypes in a standard 1:1:2 ratio, was massed on UMT-2 ultra-microbalance (Mettler-Toledo Co., Ohio, USA) and then transferred to a glass extraction vial. Whole seeds were trans-esterified in 500 ul 2.5% $H_2SO_4$ in MeOH for 3 hours at 80° C., following the method of Browse et at. (Biochem J 235:25-31, 1986) with modifications. A known amount of heptadecanoic acid was included in the reaction as an internal standard. 750 ul of water and 400 ul of hexane were added to each vial, which was then shaken vigorously and allowed to phase separate. Reaction vials were loaded directly onto GC for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30m× 0.25 mm ID, 250 um film thickness). The carrier gas was hydrogen at a constant flow of 2.5 ml/ minute. 1 ul of sample was injected in splitless mode (inlet temperature 220°C, Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis was using the Millennium Chromatography Management System (Version 3.2, Waters Corporation, Milford, Mass.). Integration and quantification were performed automatically, but all analyses were subsequently examined manually to verify correct peak identification and acceptable signal to noise ratio before inclusion of the derived results in the study.

The ACTTAG line designated W000063887 was identified as having a high oil phenotype. Specifically, fatty acids constituted 37% of seed mass, compared to 30% or less in wild type.

Example 2

Characterization of the T-DNA Insertion in Plants Exhibiting the Altered Oil Content Phenotype We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from line W000063887, and Southern blot analysis verified the genomic integration of the ACTTAG T-DNA. There appeared to be a complex T-DNA insertion, in which several T-DNAs inserted as both inverted and tandem repeats, and which included fragments of the pSKI015 backbone. Right border sequences flanked the insertion at both upstream and downstream ends. Approximately ¾ (73/101) of the T2 plants displayed the dominant herbicide resistance phenotype, which was strong evidence that the T-DNA insertions were at a single locus.

Plasmid rescue was used to recover genomic DNA flanking the T-DNA insertion, which was then subjected to sequence analysis.

The sequence flanking the downstream right T-DNA border was subjected to a basic BLASTN search and/or a search of the *Arabidopsis* Information Resource (TAIR) database (available at the arabidopsis.org website), which revealed sequence identity to P1 cloneMSD21 (GI# 4589440), mapped to chromosome 3. The downstream right border boundary was at nucleotide 2879 of P1 clone MSD21. Sequence analysis revealed that the T-DNA had inserted in the vicinity (I.e., within about 10 kb) of the gene whose nucleotide sequence is presented as SEQ ID NO: 1 and GI 4589440, complement of nucleotides 12755-12726, 12609-12203, 11579-10977, 10700-10108, 9768-9671, and which we designated ICL. Specifically, the downstream right border of the T-DNA was approximately 9.7 kb 3' to the start codon of SEQ ID NO:1.

The insertion was predicted to be dominant or semi-dominant based on T3 data, as shown in Table 1. Higher than normal oil content was observed in more than half of the T3 pools ("families") from individual T2 plants that had shown a high oil phenotype and were either homozygous or heterozygous for the ACTTAG T-DNA insertion. We used a cut-off of 32% as the threshold for "high-oil" in scoring the T3 pools (oil content in wild-type plants is ≦30% of seed mass). A score of "1" in the "High oil" column in Table 1 indicates that the particular pool was scored as high oil. Eleven of 17 lines produced high oil seed, indicating dominant or semi-dominant inheritance.

TABLE 1

Oil Content in T3 pools from individual T2 plants.

| Family # | Mean | Std Error | n= | High oil (>32%) |
|---|---|---|---|---|
| 1 | 23.5% | 1.86% | 2 | |
| 2 | 30.9% | 1.04% | 6 | |
| 3 | 35.9% | 0.62% | 3 | 1 |
| 4 | 33.7% | 1.09% | 7 | 1 |
| 5 | 30.1% | 1.00% | 3 | |
| 6 | 33.3% | 0.65% | 3 | 1 |
| 7 | 32.7% | 1.04% | 6 | 1 |
| 8 | 33.5% | 0.24% | 3 | 1 |
| 9 | 35.1% | 0.68% | 3 | 1 |
| 10 | 33.9% | 0.42% | 3 | 1 |
| 11 | 32.7% | 0.67% | 3 | 1 |
| 12 | 34.9% | 0.31% | 3 | 1 |
| 13 | 30.1% | 1.19% | 6 | |
| 14 | 30.8% | 0.17% | 3 | |
| 15 | 30.8% | 0.22% | 3 | |
| 16 | 33.8% | 0.29% | 3 | 1 |
| 17 | 32.3% | 0.69% | 3 | 1 |

Example 3

Analysis of *Arabidopsis* ICL Sequence

The amino acid sequence predicted from the ICL nucleic acid sequence is presented in SEQ ID NO:2 and GI 11994639.

Sequence analyses were performed with BLAST (Altschul et at., 1990, J. Mol. Biol. 215:403410) and PFAM (Bateman et al., 1999, Nucleic Acids Res 27:260-262), among others. BLASTP analysis indicated that the *Arabidopsis* contains a single ICL gene. (A variant predicted protein derived from the same nucleotide sequence, which differs only in the first several amino acids of the amino-terminal end, is presented in GI 15233130; the discrepancy may be based on an incorrect gene prediction.) We identified ICL (ICL) orthologs in a variety of plant species, as presented in Table 2. When the same sequences are provided in multiple Genbank entries, more than one GI number may be provided.

TABLE 2

| Species (common name) | GI number(s) | % Identity to SEQ ID NO:2 |
| --- | --- | --- |
| *Brassica napus* (canola) | 113026, 167144 | 95 |
| *Brassica napus* (canola) | 2143227 | 94 |
| *Gossypium hirsutum* (cotton) | 113029, 18486 | 84 |
| *Cucurbita maxima* (winter squash) | 8134299, 1695645 | 84 |
| *Ricinus communis* (castor bean) | 113032, 169707, 68210 | 84 |
| *Cucumis sativus* (cucumber) | 1351840, 1052578 | 84 |
| *Lycopersicon esculentum* (tomato) | 1351841, 624211 | 81 |
| *Ipomoea batatas* (sweet potato) | 12005499 | 80 |
| *Glycine max* (soybean) | 1168290, 349329 | 76 |
| *Glycine max* (soybean) | 1168289 | 76 |
| *Dendrobium crumenatum* (orchid) | 11131348 | 77 |
| *Pinus taeda* (pine) | 3831487, 1353642 | 75 |
| *Zea mays* (corn) | 1562544 (partial sequence) | 67* |
| *Oryza sativa* (rice) | 18201655 (partial sequence) | 78* |
| *Solanum tuberosum* (potato) | translation of 9250075 (EST) | 84* |

*For *Zea mays*, *Oryza sativa* and *Solanum tuberosum* sequences, percent identity calculations were performed only over the partial sequence.

While ICL mutants have been identified (Eastmond and Graham, 2000, supra), the association between ICL/ICL and an altered oil content phenotype has not previously been reported.

Example 4

Application to Molecular Breeding

The disclosed ICL gene sequences may be used as molecular probes to monitor occurrence and segregation of the ICL gene in commercial oilseed germplasm. For instance, radiolabelled ICL fragments may be used as RFLP markers (Helentjaris et al. TAG (1986) 72:761-769). The utility of RFLP markers in plant breeding is well established (Tanksley et al., Bio/Technology (1989) 7:257-264. Other sequence-based markers may be generated using the disclosed ICL sequences or closely related sequences. These include Single Nucleotide Polymorphisms (Jander et al. Plant Physiology (2002) 129: 440-450.), and cleavage amplified polymorphic DNAs (Glazebrook et al., 1998 pp173-182, in *Arabidopsis* Protocols, Humana Press Totowa, N.J.).

PCR probes designed to amplify ICL sequences may be used to quantify the expression level of ICL genes in commercial germplasm of oilseed crops. Detection of altered expression of ICL sequences can allow selection of germplasm for increased oil content.

Example 5

Constitutive Overexpression of ICL Gene Sequences in Transgenic Plants to Produce Increased Seed Oil Content Plasmids containing the *Arabidopsis* ICL gene sequence under the control of the CsVMV promoter (Verdauger et al. 1996, Plant Mol Biology 31(6):1129-1139.) were constructed (designated construct pNT-4506), and used to transform wild type *Arabidopsis*.

Oligonucleotide primers were designed to amplify the ICL gene, TAIR gene name At3g21720, from *Arabidopsis* genomic DNA. A 5' EcoRI restriction site and 3' SpeI restriction site were engineered into the primers to facilitate subcloning. The 5' primer was designed upstream of the ICL start codon and the 3' primer was designed downstream of the stop.

The ICL gene was subcloned into a cloning vector using the pCR-Script Amp Cloning Kit from Stratagene (LaJolla, Calif.). The amplified gene was verified by complete sequencing of both strands and comparing the sequence to the published Genbank sequence acc#AB025634. The 3.2 kb ICL gene was isolated from the pCR-Script Amp vector by digestion with EcoRI and SpeI and cloned into a plant expression vector(pAG-4217) containing the CsVMV promoter. The resulting plasmid, pNT-4506(CsVMV) was verified by PCR, restriction digestion and sequencing across the junctions.

Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pNT-4506 vector, which comprises T-DNA derived from the *Agrobacterium* Ti plasmid, an antibiotic resistance selectable marker gene, and the ICL coding sequence under the control of the CsVMV promoter. Individual transgenic plants were selected at the T1 generation based on antibiotic resistance and transferred to individual 2" pots to grow to maturity. An equal number of wild type (Col-0) plants were subjected to the same growth process and transplantation without selection. At flowering individual plants were fitted with an ARACONS™ (Lehle Seeds, Round Rock Texas) seed harvesting device. T2 seed was collected from individual T1 plants and wild type controls and stored in barcoded tubes for analysis. To allow non-destructive determination of oil content, Near Infrared Reflectance (NIR) spectroscopy was employed essentially as described in AOCS Procedure Am1-92 (Official Methods of the AOCS, Fifth Edition, AOCS, Champaign, Ill.). Briefly, an IFS 28/N NIR Spectrophotometer (Bruker Optics, Billerica, Mass.) was used to determine oil content as measured by AOAC Method 920.39 (Fat(Crude) or Ether Extract in Animal Feed, AOAC International, Official Methods of Analysis, 17$^{th}$ Edition, AOAC International, Gaithersburg Md.). Thirty-nine reference samples having oil contents (determined by the reference method) between 23 and 41% were subjected to NIR analysis using the IFS28/.N and used to construct a calibration curve using the manufacturer-supplied software (OPUS, Quant2, Bruker Optics, Billerica, Mass.). The correlation coefficient of the calibration was 0.9853.

Three independent spectra were taken of each T2 and controls seed pool and the resulting oil determinations for each sample were averaged. Independent transgenic events often behave differently in terms of gene expression due to a variety of factors. In practice the skilled artisan recognizes that many transgenic events produce little effect and that selections can be made from those events displaying the best performance. Despite the expectation that many of the events may have little effect as a first approximation we compared all CsVMV events with all the controls to determine if there was a significant overall difference. Table 4 shows the results of a t-test comparing means oil content of all control lines with mean oil content of all CsVMV lines. It can be seen in Table 3 that the mean oil content of the ICL events is higher than the mean oil content of the controls. This difference in mean oil content is highly statistically significant (P<0.001) for both one and two tailed tests. Comparing the top 10 pNT4506 transformants to the wild type controls indicated that seed oil content could be increased as much as 5% relative to the wild type.

TABLE 3

Comparison of Mean oil content between transgenic and control
t-Test: Two-Sample Assuming Unequal Variances

|  | Control | CsVMV |
|---|---|---|
| Mean | 37.76506977 | 38.60838462 |
| Variance | 1.266189066 | 1.521660202 |
| Observations | 43 | 52 |
| Hypothesized Mean Difference | 0 |  |
| Df | 92 |  |
| t Stat | −3.480467455 |  |
| P(T<=t) one-tail | 0.00038362 |  |
| t Critical one-tail | 1.661585429 |  |
| P(T<=t) two-tail | 0.000767239 |  |
| t Critical two-tail | 1.986086318 |  |

Example 6

Seed Specific Expression of ICL Gene Sequences in Transgenic Plants to Produce Altered Seed Oil Content Plasmids were constructed containing the *Arabidopsis* ICL gene sequence under the control of a promoter isolated from the putative cherry (*Prunus avium*) ortholog of the almond (*Prunus amygdalus*) prunin gene, which we have designated the PRU promoter (see U.S. provisional patent application no. 60/400,170), and used to transform wild type *Arabidopsis*.

Oligonucleotide primers were designed to amplify the ICL gene, TAIR gene name At3g21720, from *Arabidopsis* genomic DNA. A 5' EcoRI restriction site and 3' SpeI restriction site were engineered into the primers to facilitate subcloning. The 5' primer was designed upstream of the ICL start codon and the 3' primer was designed downstream of the stop.

The ICL gene was subcloned into a cloning vector using the pCR-Script Amp Cloning Kit from Stratagene (LaJolla, Calif.). The amplified gene was verified by sequencing both strands and comparing the sequence to the published Genbank sequence acc#AB025634. The gene was also isolated from the pCR-Script Amp vector by digestion with SmaI and SacII and cloned into a plant expression vector(pNT-4269+ MCS) containing the Pru promoter, which was digested with EcoRV and SacII. The resulting plasmid, pNT-4706(Pru) was verified by PCR, restriction digestion and sequencing across the junctions. Verification PCR primers were chosen such that the forward primer was located in the gene and the reverse primer was located in the terminator.

Comparing the PRU::ICL events with all the controls reveals an overall decrease in oil content in the transgenics that is statistically significant (P T<=t=0.03). Thus, depending on the tissue and temporal specificity of the promoter directing expression of ICL genes different and opposite effects in oil content may be created.

TABLE 4

T-test of All PRU events vs. all Controls
t-Test: Two-Sample Assuming Unequal Variances

|  | PRU:ICL | Control |
|---|---|---|
| Mean | 36.90017 | 37.76507 |
| Variance | 4.34653 | 1.266189 |
| Observations | 38 | 43 |
| Hypothesized Mean Difference | 0 |  |
| Df | 55 |  |
| t Stat | −2.28058 |  |
| P(T<=t) one-tail | 0.013236 |  |
| t Critical one-tail | 1.673034 |  |
| P(T<=t) two-tail | 0.026471 |  |
| t Critical two-tail | 2.004044 |  |

Example 7

Constitutive Overexpression of a *Glycine max* ICL Gene Sequence in Transgenic Plants to Produce Increased Seed Oil Content Plasmids containing a *Glycine max* ICL gene sequence under the control of the CsVMV promoter (Verdauger et al. 1996, Plant Mol Biology 31(6)1129-1139.) were constructed (designated construct pNT-4508), and used to transform wild type *Arabidopsis*. RNA was extracted from soybean cotyledons 3 days post imbibition using Tri Reagent (Product number T9424, Molecular Research Center, Inc.). The RNA was reverse transcribed using a mixture of oligonucleotide GmI-CLR1 and oligo(dT)13 with Promega MMLV-RT(Product number M1701). The GmICL gene was amplified from the cDNA using the Expand High Fidelity PCR System from Roche and the GmICL1_F and GmICL1_R primer set.

```
GmICL1_F
5'-CCATGGCTGCATCATTATTTATG-3'        (SEQ ID NO: 3)

GmICL1_R
5'-CACTTTCACATTCTGGCCTTAG-3'         (SEQ ID NO: 4)

GmICLR1
5'-                                  (SEQ ID NO: 5)
TCACATTCTGGCCTTAGCAACCACAATACTGC-3'
```

The GmICL PCR product was cloned using the pCR2.1 TA Cloning Kit from Invitrogen(Product number K2000-01). The amplified gene was verified by sequencing both the upper and lower strands and comparing the sequence to cDNA contigs that were constructed from ESTs and partial cDNA sequences. The gene was determined to be GmICL2. The 1.7 kb GmICL2 gene was isolated from the pCR2.1 vector by digestion with EcoRI. The gene was cloned into a plant expression vector containing the CsVMV promoter(pAG-4217) which was also digested with EcoRI and dephosphorylated with Shrimp Alkaline Phosphatase(Roche, Product number 1758250).

Standard methods were used for the generation of *Arabidopsis* transgenic plants, and were essentially as described in Example 5. Oil content was determined by NIR essentially as described in Example 5.

Three independent spectra are taken of each T2 and controls seed pool and the resulting oil determinations for each sample are averaged. Oil Contents for CsVMV transgenics and Col-0 controls can then be compared and high oil events selected for further propagation.

Expression of a *Glycine max* and *Arabidopsis* ICL Gene sequences in Transgenic Plants Under the Control of Tissue Specific Promoters Plasmids containing the *Arabidopsis* ICL gene sequence or *Glycine max* ICL (GmICL) sequence under the control of the PRU promoter (the associated promoter sequence recovered from the putative cherry (*Prunus avium*) orthologs of the almond (*Prunus amygdalus*) prunin gene, designated as the PRU promoter.), or other tissue specific promoters of choice are created using standard methods. For instance, the GmICL2 gene is isolated from the pCR2.1 vector by digestion with BamHI and EcoRV and cloned into the Gateway entry vector pENTR1A also digested with BamHI and EcoRV. The GmICL2 gene is then cloned into a plant expression vector(pNT-4287) containing the Pru promoter using the Gateway System (Invitrogen) according to the manufacturers instructions. pNT-4287 is converted into a Gateway destination vector by the addition of a Gateway Reading Frame. The *Arabidopsis* ICL gene is isolated from the pCR-Script Amp vector by digestion with SmaI and SacII and cloned into a plant expression vector(pNT-4269+MCS) containing the Pru promoter which was digested with EcoRV and SacII. Both SmaI and EcoRV are blunt cutters. The resulting plasmids, pNT-4708 (PRU-GmICL) and pNT-4706(Pru-Hio1.4 *Arabidopsis thaliana*) are verified by PCR, restriction digestion and sequencing across the junctions. Verification PCR primers were chosen such that the forward primer was located in the gene and the reverse primer was located in the terminator.

Standard methods are used for the generation of *Arabidopsis* transgenic plants, and are essentially as described in Example 5. Oil content is determined by NIR essentially as described in Example 5.

Three independent spectra are taken of each T2 and controls seed pool and the resulting oil determinations for each sample are averaged. Oil Contents for CsVMV transgenics and Col-0 controls can then be compared and high oil transgenic events selected for further propagation.

REFERENCES

Altschul, S. F. et al., *J. Mol. Biol.* 215:403-410, 1990.
Ausubel F M et al. Current Protocols in Molecular Biology, John Wiley & Sons, New York, N.Y., 1993.
Baldwin D et al., *Cur Opin Plant Biol.* 2(2):96-103, 1999.
Bateman et al., 1999, Nucleic Acids Res 27:260-262 (website at pfam.wustl.edu).
Baulcombe D, *Arch Virol Suppl* 15:189-201, 1999.
Cannon et al., Plant Molec. Biol. (1990) 15:39-47.
Ch'ng et al., Proc. Natl. Acad. Sci. USA (1989) 86:10006-10010
Christou et al., Proc. Natl. Acad. Sci USA (1989) 86:7500-7504.
De Block et al., Plant Physiol. (1989) 91:694-701.
Dieffenbach C and Dveksler G (Eds.) PCR Primer: A Laboratory Manual, Cold Spring Harbor Laboratory Press, NY, 1989.
Everett et al., Bio/Technology (1987) 5:1201
Feldmann et al., Science 243: 1351-1354, 1989.
Focks N and Benning C, Plant Physiol 118:91-101, 1998.
Fridborg I et al., Plant Cell 11: 1019-1032, 1999.
Harlow E and Lane D, Antibodies: A Laboratory Manual, Cold Spring Harbor Laboratory Press, 1988, New York.
Harlow E and Lane D, Using Antibodies: A Laboratory Manual, Cold Spring Harbor Laboratory Press, 1999, New York
Hayashi H et al., Science 258: 1350-1353, 1992.
James D W and Dooner H K (1990) Theor Appl Genet 80, 241-245.
Jones J D et al, Transgenic Res 1:285-297 1992.
Kardailsky I et al., Science 286: 1962-1965, 1999.
Kline et al., Nature (1987) 327:70.
Kunkel T A et al., Methods Enzymol. 204:125-39, 1991.
Lemieux B et al., 1990, Theor Appl Genet 80, 234-240.
Nakamura Y et al., 1999, Nucleic Acids Res 27:292.
Napoli, et al., Plant Cell 2:279-289, 1990.
Sambrook et al. Molecular Cloning: A Laboratory Manual (Second Edition), Cold Spring Harbor Press, Plainview, N.Y., 1989.
Schaffer R, et al., Cell 93: 1219-1229, 1998.
Sheehy et al., Proc. Natl. Acad. Sci. USA (1988) 85:8805-8809.
Smith, et al., Nature 334:724-726, 1988.
Smith et al., Mol. Gen. Genetics (1990) 224:477-481.
van der Krol et al., Biotechniques (1988) 6:958-976.
van der Krol et al., The Plant Cell (1990) 2:291-299.
Van Haaren M J J et al., Plant Mol Bio 21:625-640, 1993.
Verdaguer B et al., Plant Mol Biol 37:1055-1067, 1998.
Waterhouse, et al., Proc. Natl. Acad. Sci. USA 95:13959-13964, 1998.
Weigel D, et al., Plant Physiology, 122:1003-1013, 2000.
Wilson K et al., Plant Cell 8: 659-671, 1996.
Yadav N S et al,. Plant Physiol 103, 467-476 (1993).

It is claimed:

1. A method of producing an altered oil content phenotype in a plant, said method comprising:
   a) introducing into progenitor cells of the plant a plant transformation vector comprising a CsVMV promoter and a nucleotide sequence that encodes a sequence that encodes an isocitrate lysase (ICL) polypeptide,
   b) growing the transformed progenitor cells to produce a transgenic plant, wherein said polynucleotide sequence is expressed, and
   c) identifying said transgenic plant with an altered oil content phenotype by measuring the oil content in said transgenic plant and comparing it to that of the oil content measured in a control plant.

2. The method of claim 1 wherein the ICL polypeptide has at least 50% sequence identity to the amino acid sequence presented as SEQ ID NO:2, and wherein the sequence comprises an isocitrate lyase domain.

3. The method of claim 1 wherein the ICL polypeptide has at least 80% sequence identity to the amino acid sequence presented as SEQ ID NO:2.

4. The method of claim 1 wherein the ICL polypeptide has at least 90% sequence identity to the amino acid sequence presented as SEQ ID NO:2.

5. The method of claim 1 wherein the ICL polypeptide has the amino acid sequence presented as SEQ ID NO:2.

6. The method of claim 1 wherein an ICL polypeptide is over-expressed in the transgenic plant, and wherein the altered oil content phenotype is a high oil phenotype.

7. A plant obtained by a method of claim 6, wherein the ICL polypeptide has greater than 95% sequence identity to the amino acid sequence presented as SEQ ID NO:2.

8. The plant of claim 7, which is selected from the group consisting of rapeseed, soy, corn, sunflower, cotton, cocoa, safflower, oil palm, coconut palm, flax, castor and peanut.

9. A plant part obtained from a plant according to claim 7.

10. The plant part of claim 9, which is a seed.

11. A transgenic plant comprising a chimeric DNA construct comprising a CsVMV promoter and a DNA encoding an isocitrate lysase (ICL) polypeptide, wherein the ICL polypeptide has greater than 95% sequence identity to the amino acid sequence presented as SEQ ID NO:2, whereby the transgenic plant has an increased level of ICL relative to a non-transgenic plant and wherein oil from the plant has increased content compared to a plant lacking the chimeric DNA construct.

12. A method of improving the oil content produced from a plant, said method comprising:

a) introducing into a plant a chimeric DNA construct comprising a plant specific transcription initiation region, a CsVMV promoter and a DNA encoding an isocitrate lysase (ICL) which, when introduced into cells of said plant increases ICL activity in an amount sufficient to increase the quantity of oil produced by the plant compared to a plant lacking the chimeric DNA construct b) identifying said plant with an increased oil content by measuring the oil content in said plant and comparing it to that of the oil content measured in the plant lacking the chimeric DNA construct, thereby providing a method of improving the oil content produced from a plant.

13. The method according to claim 12, wherein the DNA encoding ICL is from a plant selected from the group consisting of rapeseed, soy, corn, sunflower, cotton, cocoa, safflower, oil palm, flax, castor and peanut.

* * * * *

UNITED STATES PATENT AND TRADEMARK OFFICE
CERTIFICATE OF CORRECTION

PATENT NO. : 7,476,779 B2
APPLICATION NO. : 10/508442
DATED : January 13, 2009
INVENTOR(S) : Lightner et al.

It is certified that error appears in the above-identified patent and that said Letters Patent is hereby corrected as shown below:

Column 4, Line 31, "progagules" should be --propagules--.

Column 4, Lines 43-44, "genotypically plant" should be --genotypically similar plant--.

Column 6, Line 4, "fill-length" should be --full-length--.

Column 6, Line 21, "one of more of" should be --one or more of--.

Column 6, Line 32, "plan" should be --pfam--.

Column 6, Lines 33-34, "SEQ ED" should be --SEQ ID--.

Column 6, Line 38, "one of more of" should be --one or more of--.

Column 7, Line 45, "blast README" should be --blast/README--.

Column 9, Line 1, "Haynen" should be --Huynen--.

Column 9, Line 56, "nucleic acid" should be --nucleic acid.--.

Column 9, Line 59, "of in plant cells" should be --of plant cells--.

Column 9, Line 63, "from least one" should be --from at least one--.

Column 10, Line 43, "bombardment calcium-phosphate--DNA" should be --bombardment, calcium-phosphate-DNA--.

Column 11, Line 3, "sunflower Everett" should be --sunflower (Everett--.

UNITED STATES PATENT AND TRADEMARK OFFICE
CERTIFICATE OF CORRECTION

PATENT NO. : 7,476,779 B2
APPLICATION NO. : 10/508442
DATED : January 13, 2009
INVENTOR(S) : Lightner et al.

It is certified that error appears in the above-identified patent and that said Letters Patent is hereby corrected as shown below:

Column 11, Line 53, "32740" should be --327-40--.

Column 13, Line 21, "follows methods" should be --following methods--.

Column 13, Line 27, "500ul/750ul/400ul/1ul" should be --500µl/750µl/400µl/1µl--.

Column 13, Line 28, "et at." should be --et al.--.

Column 13, Line 31, "500ul/750ul/400ul/1ul" should be --500µl/750µl/400µl/1µl--.

Column 13, Line 39, "250um" should be --250µm--.

Column 13, Line 40, "500ul/750ul/400ul/1ul" should be --500µl/750µl/400µl/1µl--.

Column 13, Line 41, "220□C" should be --220°C--.

Column 13, Line 55, "W000063887" should be --WO00063887--.

Column 14, Line 4, "W000063887" should be --WO00063887--.

Column 14, Line 26, "Le." should be --i.e.--.

Column 15, Line 8, "403410" should be --403-410--.

Column 15, Line 8, "et at." should be --et al.--.

Column 15, Line 63, "7:257-264" should be --7:257-264)--.

Column 20, Line 42, "Verdaguer" should be --Verdauger--.

UNITED STATES PATENT AND TRADEMARK OFFICE
CERTIFICATE OF CORRECTION

PATENT NO.         : 7,476,779 B2
APPLICATION NO.    : 10/508442
DATED              : January 13, 2009
INVENTOR(S)        : Lightner et al.

It is certified that error appears in the above-identified patent and that said Letters Patent is hereby corrected as shown below:

Column 25, Line 49 (in Claim 1), "lysase" should be --lyase--.

Column 26, Line 59 (in Claim 11), "lysase" should be --lyase--.

Column 27, Line 4 (in Claim 12), "lysase" should be --lyase--.

Signed and Sealed this

Third Day of November, 2009

David J. Kappos
*Director of the United States Patent and Trademark Office*

SEQUENCE LISTING

<160> NUMBER OF SEQ ID NOS: 5

<210> SEQ ID NO 1
<211> LENGTH: 1731
<212> TYPE: DNA
<213> ORGANISM: Arabidopsis thaliana

<400> SEQUENCE: 1

```
atggctgcat ctttctctgt ccctctatg ataatggaag aagaagggag attcgaagcg      60
gaggttgcgg aagtgcagac ttggtggagc tcagagaggt tcaagctaac aaggcgccct     120
tacactgccc gtgacgtggt ggctctacgt ggccatctca agcaaggcta tgcttcgaac     180
```

```
gagatggcta agaagctgtg gagaacgctc aaaagccatc aagccaacgg tacggcctct    240
cgcaccttcg gagcgttgga ccctgttcag gtgaccatga tggctaaaca tttggacacc    300
atctatgtct ctggttggca gtgctcgtcc actcacacat ccactaatga gcctggtcct    360
gatcttgctg attatccgta cgacaccgtt cctaacaagg ttgaacacct cttcttcgct    420
cagcagtacc atgacagaaa gcagagggag gcaagaatga gcatgagcag agaagagagg    480
acaaaaactc cgttcgtgga ctacctaaag cccatcatcg ccgacggaga caccggcttt    540
ggcggcacca ccgccaccgt caaactctgc aagcttttcg ttgaaagagg cgccgctggg    600
gtccacatcg aggaccagtc ctccgtcacc aagaagtgtg ccacatggc cggaaaggtc    660 ctcgtggcag tcagcgaaca catcaaccgc cttgtcgcgg ctcggctcca gttcgacgtg    720
atgggtacag agaccgtcct tgttgctaga acagatgcgg tcgcagctac tctgatccag    780
tcgaacattg acgcgaggga ccaccagttc atcctcggtg ccactaaccc gagccttaga    840
ggcaagagtt tgtcctcgct tctggctgag ggaatgactg taggcaagaa tggtccggcg    900
ttgcaatcca ttgaagatca gtggcttggc tcggccggtc ttatgacttt ctcggaagct    960
gtcgtgcagg ccatcaagcg catgaacctc aacgagaacg agaagaatca gagactgagc    1020
gagtggttaa cccatgcaag gtatgagaac tgcctgtcaa atgagcaagg ccgagtgtta    1080
gcagcaaaac ttggtgtgac agatcttttc tgggactggg acttgccgag aaccagagaa    1140
ggattctacc ggttccaagg ctcggtcgca gcggccgtgg tccgtggctg ggcctttgca    1200
cagatcgcag acatcatctg gatggaaacg gcaagccctg atctcaatga atgcacccaa    1260
ttcgccgaag gtatcaagtc caagacaccg gaggtcatgc tcgcctacaa tctctcgccg    1320
tccttcaact gggacgcttc cggtatgacg gatcagcaga tggttgagtt cattccgcgg    1380
attgctaggc tcggatattg ttggcagttc ataacgcttg cgggtttcca tgcggatgct    1440
cttgtggttg atacatttgc aaaggattac gctaggcgcg ggatgttggc ttatgtggag    1500
aggatacaaa gagaagagag gacccatggg gttgacactt tggctcacca gaaatggtcc    1560
ggtgctaatt actatgatcg ttatcttaag accgtccaag gtggaatctc ctccactgca    1620
gccatgggaa aaggtgtcac tgaagaacag ttcaaggaga gttggacaag gccgggagct    1680
gatggaatgg gtgaagggac tagccttgtg gtcgccaagt caagaatgta a              1731
```

<210> SEQ ID NO 2
<211> LENGTH: 576
<212> TYPE: PRT
<213> ORGANISM: Arabidopsis thaliana

<400> SEQUENCE: 2

Met Ala Ala Ser Phe Ser Val Pro Ser Met Ile Met Glu Glu Glu Gly
1               5                   10                  15

Arg Phe Glu Ala Glu Val Ala Glu Val Gln Thr Trp Trp Ser Ser Glu
            20                  25                  30

Arg Phe Lys Leu Thr Arg Arg Pro Tyr Thr Ala Arg Asp Val Val Ala
        35                  40                  45

Leu Arg Gly His Leu Lys Gln Gly Tyr Ala Ser Asn Glu Met Ala Lys
    50                  55                  60

Lys Leu Trp Arg Thr Leu Lys Ser His Gln Ala Asn Gly Thr Ala Ser
65                  70                  75                  80

Arg Thr Phe Gly Ala Leu Asp Pro Val Gln Val Thr Met Met Ala Lys
                85                  90                  95

His Leu Asp Thr Ile Tyr Val Ser Gly Trp Gln Cys Ser Ser Thr His

-continued

```
              100                 105                 110
Thr Ser Thr Asn Glu Pro Gly Pro Asp Leu Ala Asp Tyr Pro Tyr Asp
        115                 120                 125

Thr Val Pro Asn Lys Val Glu His Leu Phe Phe Ala Gln Gln Tyr His
    130                 135                 140

Asp Arg Lys Gln Arg Glu Ala Arg Met Ser Met Ser Arg Glu Glu Arg
145                 150                 155                 160

Thr Lys Thr Pro Phe Val Asp Tyr Leu Lys Pro Ile Ile Ala Asp Gly
                165                 170                 175

Asp Thr Gly Phe Gly Gly Thr Thr Ala Thr Val Lys Leu Cys Lys Leu
            180                 185                 190

Phe Val Glu Arg Gly Ala Ala Gly Val His Ile Glu Asp Gln Ser Ser
                195                 200                 205

Val Thr Lys Lys Cys Gly His Met Ala Gly Lys Val Leu Val Ala Val
    210                 215                 220

Ser Glu His Ile Asn Arg Leu Val Ala Ala Arg Leu Gln Phe Asp Val
225                 230                 235                 240

Met Gly Thr Glu Thr Val Leu Val Ala Arg Thr Asp Ala Val Ala Ala
                245                 250                 255

Thr Leu Ile Gln Ser Asn Ile Asp Ala Arg Asp His Gln Phe Ile Leu
            260                 265                 270

Gly Ala Thr Asn Pro Ser Leu Arg Gly Lys Ser Leu Ser Ser Leu Leu
        275                 280                 285

Ala Glu Gly Met Thr Val Gly Lys Asn Gly Pro Ala Leu Gln Ser Ile
    290                 295                 300

Glu Asp Gln Trp Leu Gly Ser Ala Gly Leu Met Thr Phe Ser Glu Ala
305                 310                 315                 320

Val Val Gln Ala Ile Lys Arg Met Asn Leu Asn Glu Asn Glu Lys Asn
                325                 330                 335

Gln Arg Leu Ser Glu Trp Leu Thr His Ala Arg Tyr Glu Asn Cys Leu
            340                 345                 350

Ser Asn Glu Gln Gly Arg Val Leu Ala Ala Lys Leu Gly Val Thr Asp
        355                 360                 365

Leu Phe Trp Asp Trp Asp Leu Pro Arg Thr Arg Glu Gly Phe Tyr Arg
    370                 375                 380

Phe Gln Gly Ser Val Ala Ala Val Val Arg Gly Trp Ala Phe Ala
385                 390                 395                 400

Gln Ile Ala Asp Ile Ile Trp Met Glu Thr Ala Ser Pro Asp Leu Asn
                405                 410                 415

Glu Cys Thr Gln Phe Ala Glu Gly Ile Lys Ser Lys Thr Pro Glu Val
            420                 425                 430

Met Leu Ala Tyr Asn Leu Ser Pro Ser Phe Asn Trp Asp Ala Ser Gly
        435                 440                 445

Met Thr Asp Gln Gln Met Val Glu Phe Ile Pro Arg Ile Ala Arg Leu
    450                 455                 460

Gly Tyr Cys Trp Gln Phe Ile Thr Leu Ala Gly Phe His Ala Asp Ala
465                 470                 475                 480

Leu Val Val Asp Thr Phe Ala Lys Asp Tyr Ala Arg Arg Gly Met Leu
                485                 490                 495

Ala Tyr Val Glu Arg Ile Gln Arg Glu Glu Arg Thr His Gly Val Asp
            500                 505                 510

Thr Leu Ala His Gln Lys Trp Ser Gly Ala Asn Tyr Tyr Asp Arg Tyr
        515                 520                 525
```

-continued

```
Leu Lys Thr Val Gln Gly Gly Ile Ser Ser Thr Ala Ala Met Gly Lys
        530                 535                 540

Gly Val Thr Glu Glu Gln Phe Lys Glu Ser Trp Thr Arg Pro Gly Ala
545                 550                 555                 560

Asp Gly Met Gly Glu Gly Thr Ser Leu Val Val Ala Lys Ser Arg Met
                565                 570                 575

<210> SEQ ID NO 3
<211> LENGTH: 23
<212> TYPE: DNA
<213> ORGANISM: Artificial
<220> FEATURE:
<223> OTHER INFORMATION: Oligonucleotide

<400> SEQUENCE: 3
ccatggctgc atcattattt atg                                    23

<210> SEQ ID NO 4
<211> LENGTH: 22
<212> TYPE: DNA
<213> ORGANISM: Artificial
<220> FEATURE:
<223> OTHER INFORMATION: Oligonucleotide

<400> SEQUENCE: 4
cactttcaca ttctggcctt ag                                     22

<210> SEQ ID NO 5
<211> LENGTH: 32
<212> TYPE: DNA
<213> ORGANISM: Artificial
<220> FEATURE:
<223> OTHER INFORMATION: Oligonucleotide

<400> SEQUENCE: 5
tcacattctg gccttagcaa ccacaatact gc                          32
```